United States Patent [19]

Winiewski

[11] Patent Number: 5,035,020

[45] Date of Patent: Jul. 30, 1991

[54] ROTARY TOOTHBRUSH

[76] Inventor: Gerald Winiewski, 6447 Laurentian Way S.W., Calgary, Alberta, Canada, T3E 5N2

[21] Appl. No.: 552,941

[22] Filed: Jul. 16, 1990

[30] Foreign Application Priority Data

Sep. 29, 1989 [CA] Canada .................................. 614979

[51] Int. Cl.⁵ .......................... A46B 13/02; A46B 9/04
[52] U.S. Cl. ........................................................ 15/23
[58] Field of Search ............................. 15/23, 24, 22.1

[56] References Cited

U.S. PATENT DOCUMENTS

| | | | |
|---|---|---|---|
| 1,374,181 | 4/1921 | Bohlman | 15/23 |
| 1,570,465 | 1/1926 | D'Aprea | 15/23 |
| 2,758,326 | 8/1956 | Keely et al. | 15/23 |
| 4,275,749 | 6/1981 | Caroli | 15/23 |

FOREIGN PATENT DOCUMENTS 3544256  6/1987  Fed. Rep. of Germany ....... 15/22.1

Primary Examiner—Edward L. Roberts
Attorney, Agent, or Firm—George Haining Dunsmuir

[57] ABSTRACT

The conventional electric toothbrush includes a vibrating head or cylindrical brushes which rotate in one direction only. The toothbrush described herein includes a plurality of annular brushes which rotate in opposite directions to simulate the up and down brushing action of ordinary, manually operated toothbrushes.

4 Claims, 5 Drawing Sheets

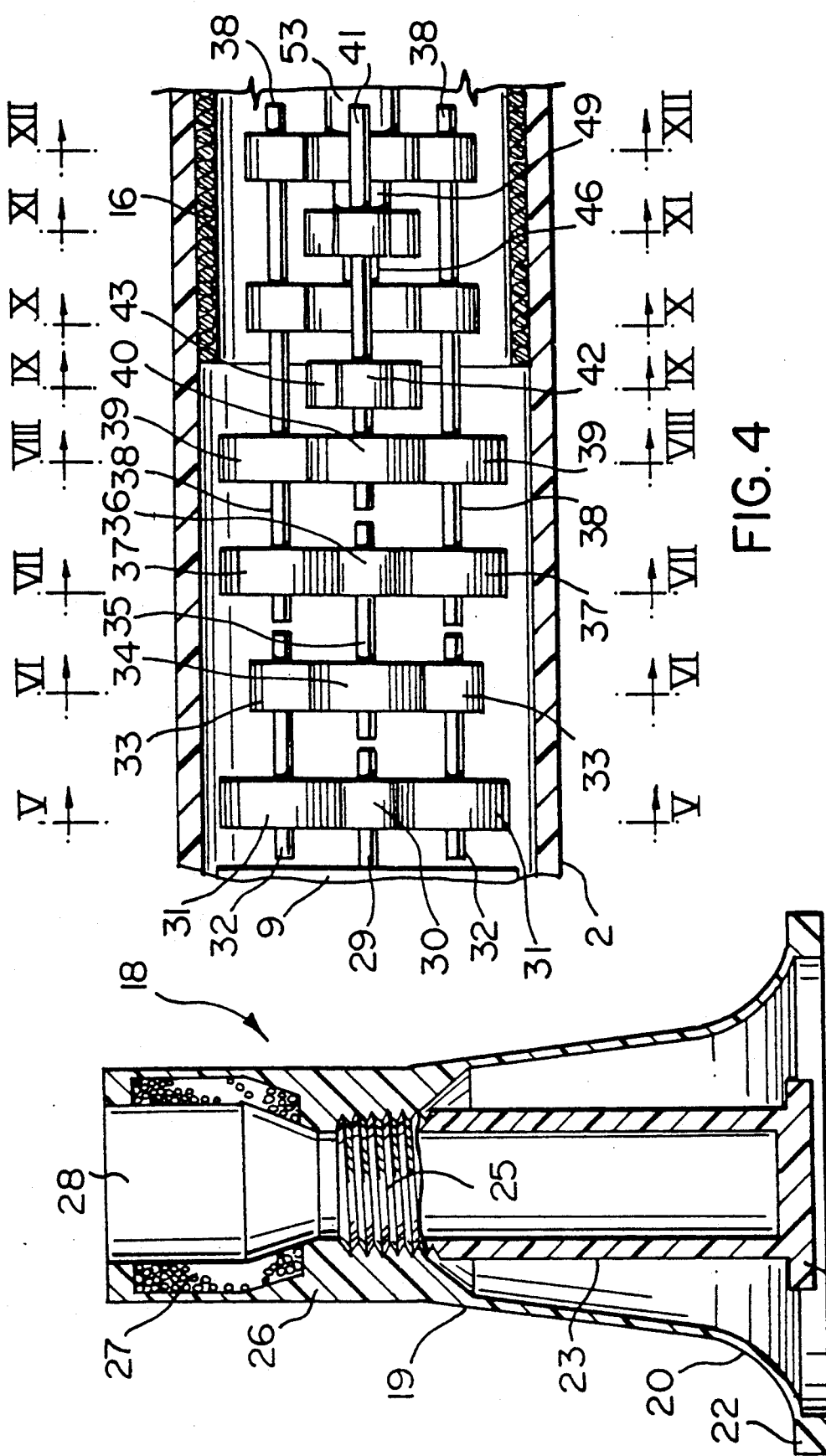

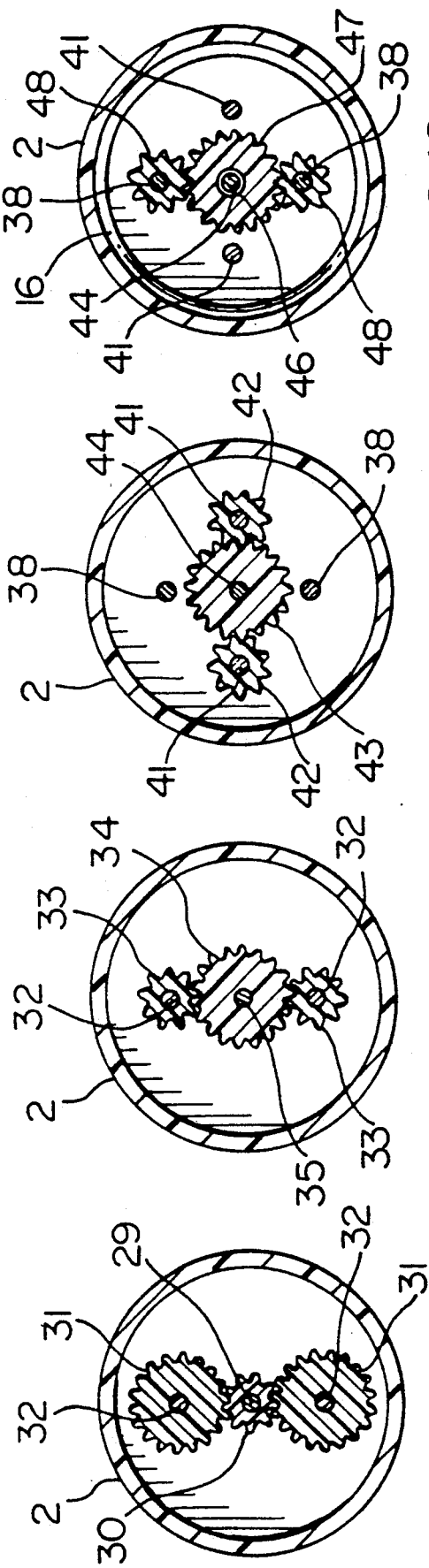
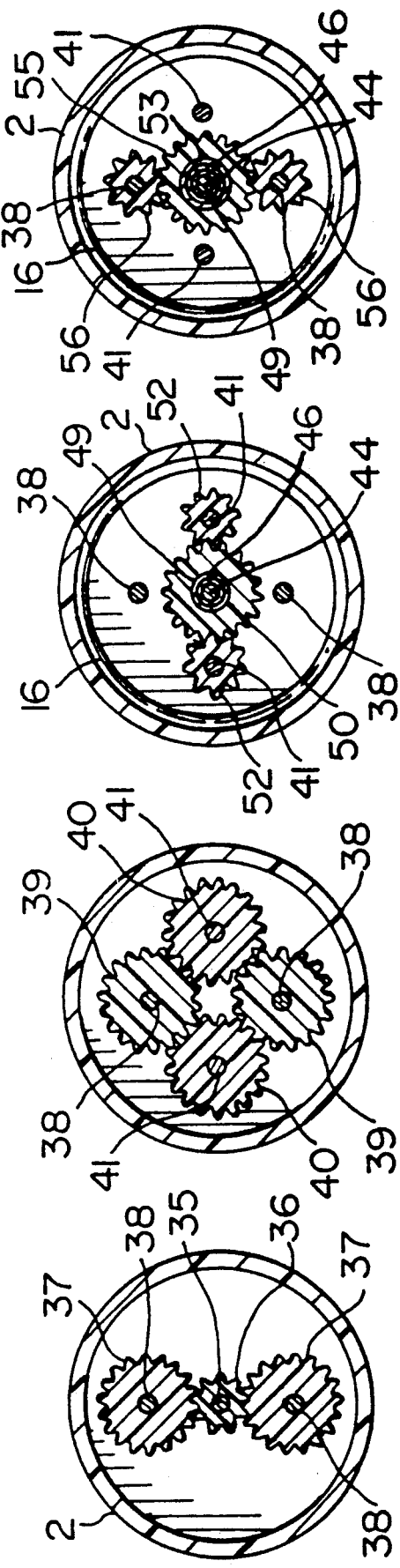

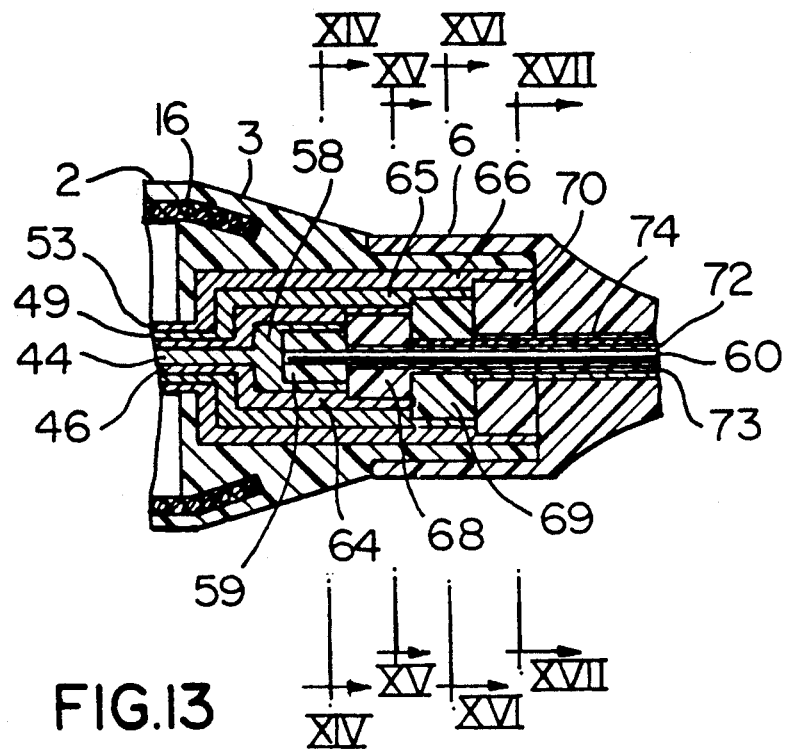
FIG.13
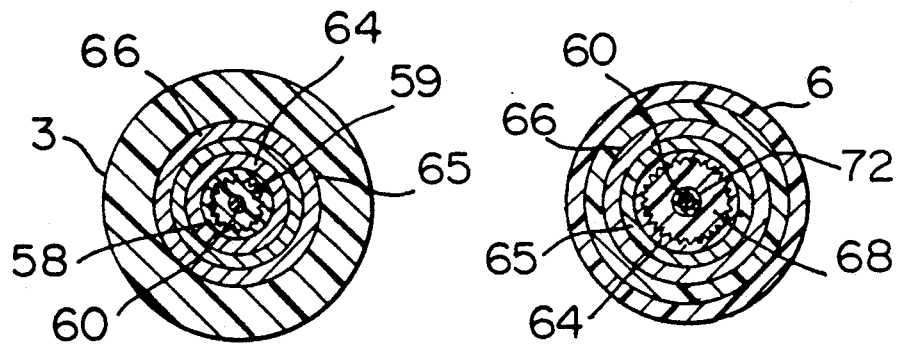
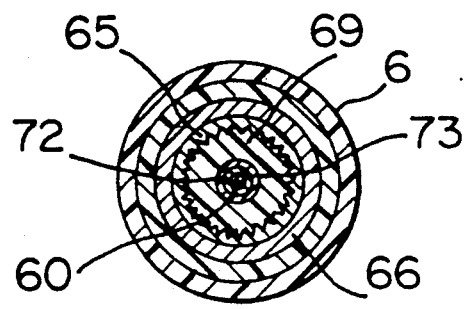
FIG.14  FIG.15
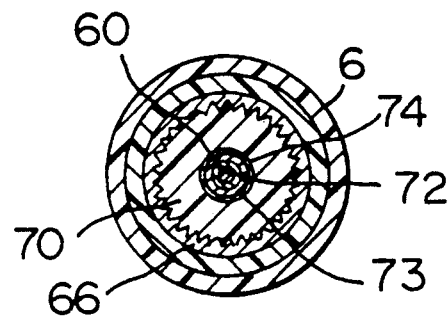
FIG.16  FIG.17

ROTARY TOOTHBRUSH

BACKGROUND OF THE INVENTION

This invention relates to a toothbrush, and in particular to a so-called electric toothbrush of the rotary type.

In general, currently available electro-mechanical toothbrushes are, in effect, conventional toothbrushes mounted to vibrate in handles. When used as directed, such devices are not as effective as conventional hand held and operated toothbrushes. A need exists for an electromechanical (commonly referred to as "electric") toothbrush, the bristles of which perform the vertical reciprocating or up and down brushing action recommended by dentists.

The object of the present invention is to meet the above described need by providing a relatively simple rotary toothbrush, which simulates the up and down or vertical reciprocating action of a conventional manually operated toothbrush.

BRIEF SUMMARY OF THE INVENTION

Accordingly, the present invention relates to a rotary toothbrush comprising elongated casing means; a plurality of annular brush means rotatably mounted in one at least partially open end of said casing means for rotation around a single axis; drive means in the casing means for rotating said brush means; and transmission means connecting said drive means to said brush means for rotating at least one said brush means in one direction, and rotating at least one other said brush means in the opposite direction.

BRIEF DESCRIPTION OF THE DRAWINGS

The invention is described in greater detail hereinafter with reference to the accompanying drawings, which illustrate a preferred embodiment of the invention, and wherein:

FIG. 3 is a longitudinal sectional view of a charging stand for use with the toothbrush of FIGS. 1 and 2;

FIG. 4 is a schematic, longitudinal sectional view of a portion of a casing of the toothbrush of FIGS. 1 and 2, illustrating a transmission;

FIGS. 5 to 12 are cross sections taken generally along lines V—V to XII—XII, respectively of FIG. 4;

FIG. 13 is a schematic, longitudinal sectional view of another portion of the toothbrush casing;

FIGS. 14 to 17 are cross sections taken generally along lines XIV to XVII, respectively of FIG. 13;

DESCRIPTION OF THE PREFERRED EMBODIMENT(S)

Figures 1, 2:
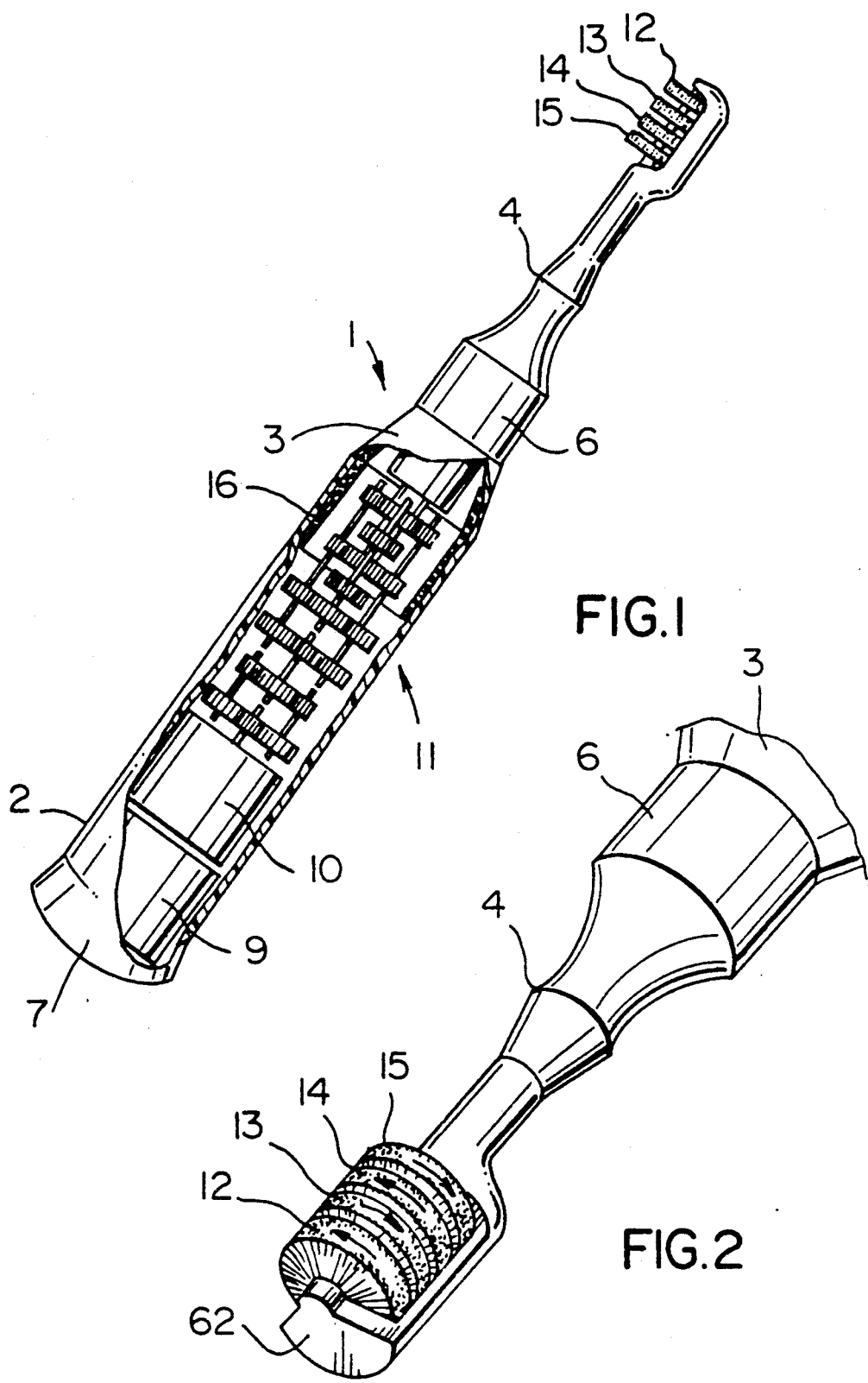
FIG. 1 is a partly sectioned, perspective view of a toothbrush in accordance with the present invention.
FIG. 2 is a perspective view of the brush end of the toothbrush of FIG. 1.

It will be appreciated that for the sake of simplicity the toothbrush is illustrated schematically, with parts omitted. For example, electrical connections between various elements have been completely omitted.

With reference to the drawings, the toothbrush of the present invention includes an elongated generally cylindrical casing generally indicated at 1. The casing 1 is defined by a cylindrical handle 2 with a tapering shoulder 3 at the top end thereof which is connected to a detachable brush carrier 4 by inserting the reduced diameter top end of the handle 2 into a cylindrical socket defined by the bottom end 6 of the brush carrier 4 (FIG. 13). The bottom end 7 of the handle 2 is convex and slightly larger in diameter than the remainder of the handle, so that the device cannot be left standing on end, and to prevent insertion of the wrong end of the device into a charging stand (FIG. 3).

The basic elements of the toothbrush housed by the casing 1 include a battery 9, a D.C. motor 10, a transmission generally indicated at 11 and a plurality of annular brushes 12, 13, 14 and 15. The battery 9 is rechargeable, typically including six Ni-Cad dry cells.

For such purpose a wire coil 16 (FIGS. 1, 10, 11, 12 and 13) is provided in the upper end of the handle 2 for use when charging the battery 9. A charging stand generally indicated at 18 (FIG. 3) is provided with the toothbrush. The stand 18 includes a tubular casing 19 with a bottom end or skirt 20, which flares outwardly to an annular base 22. A tubular brush-receiving socket 23 with a closed bottom end 24 is provided in the casing 19. The top end 25 of the socket 23 is externally threaded for connecting the latter to the threaded central portion 26 of the casing 19. A wire coil 27 is mounted in the top end of the casing 19 for inducing a charging current in the coil 16. The shape of the interior of the top end of the casing 19 is complementary to the shape of the shoulder 3 and the coupler 6 of the casing 1. The diameter of the opening 28 in the top end of the casing 19 is large enough to admit the top end of the toothbrush, but too small to admit the flanged bottom end 7 of the handle 2.

As best shown in FIGS. 4 to 12, the shaft 29 of the motor 10 is connected to a spur gear 30, which drives a pair of similar larger gears 31 (FIG. 5). The gears 31 are connected to one end of a pair of shafts 32, which also carries a pair of smaller spur gears 33 for driving a central gear 34 (FIG. 6). The central gear 34 carries a shaft 35, which is also connected to a small central gear 36 (FIG. 7) for rotating a pair of larger spur gears 37. Shafts 38 extending out of the gears 37 drive two gears 39 of a four gear set. The gears 39 mesh with two other gears 40 of the four gear set (FIG. 8). It will be noted that the gears 39 and 40 are in the same plane, and that a line through the centers of the gears 39 is perpendicular to a line through the centers of the gears 40. The gears 40 carry shafts 41. The shafts 38 and 41 extend through the remainder of the transmission 11. The shafts 41 carry gears 42 for rotating a larger central gear 43 (FIG. 9). The gear 43 is connected to one end of a shaft 44 which is intended to rotate the outermost annular brush. The shaft 44 extends through a sleeve 46 in a central gear 47 which is driven by a pair of smaller gears 48 mounted on the shafts 38 (FIG. 10). The sleeve 46 is free to rotate with respect to the shaft 44, but is connected to the gear 47 for rotation therewith. Continuing to move toward the brushes end of the transmission 11, the shaft 44 and the sleeve 46 extend into a sleeve 49 in a large central gear 50, which is driven by a pair of small spur gears 5 on the shafts 41. The sleeve 49 is free to rotate with respect to the sleeve 46, but is connected to the gear 50. Similarly the shaft 44 and the sleeves 46 and 49 extend through a sleeve 53 in a large central gear 55, which is driven by smaller spur gears 56 mounted on the shafts 38 (FIG. 11). The sleeve 53 is free to rotate with respect to the sleeve 49, but is connected to the gear 55.

Because the small gears 42, 48, 52 and 56 are all the same size, and the same is true of the large gears 43, 47, 50 and 55, the shafts 38 and 41 are driven at the same speed. However, because of the four gear arrangement defined by the gears 39 and 40, the shafts 38 and 41, and consequently the gears which they carry rotate in opposite directions.

Thus, it will be noted that the shaft 44 and the sleeve 49 are driven in the same direction and at the same speed, while the sleeves 46 and 53 are driven in the opposite direction and at the same speed as each other and as the shaft 44 and the sleeve 49.

Figure 18:
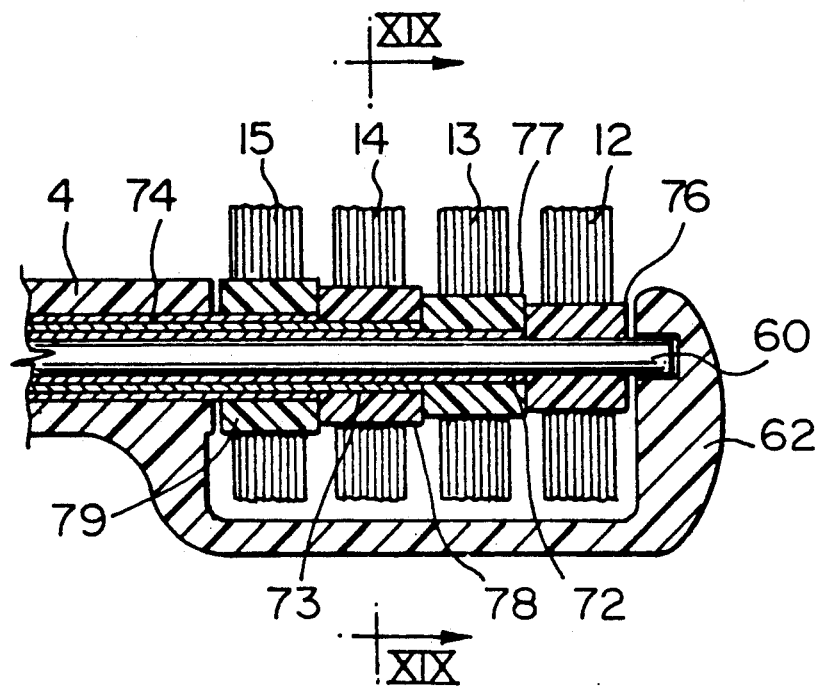
FIG. 18 is a longitudinal sectional view of the brush end of the toothbrush of FIGS. 1 and 2.

Referring to FIGS. 13 to 18, the shaft 44 extends into one end of a cup-shaped coupler 58 which includes internal, longitudinally extending, alternating teeth and troughs for mating with the teeth on a cylindrical gear 59. The gear 59 is mounted on one end of a shaft 60, which extends through the brush carrier 4 to the outer free end 62 thereof. Similarly, the sleeves 46, 49 and 53 extend into the closed ends of cup-like couplers 64, 65 and 66, respectively, which are co-axial with the coupler 58. Like the coupler 58, the couplers 64, 65 and 66 include internal, longitudinally extending alternating teeth and grooves for mating with the longitudinally extending teeth on cylindrical gears 68, 69 and 70. The gears 68, 69 and 70 are mounted on the ends of tubular shafts 72, 73 and 74, respectively which extend through the brush carrier 4. Referring to FIG. 18 at the outer free end of the brush carrier 4, the shaft 60 extends through the hub 76 of the brush 12, and the shafts 72, 73 and 74 extend into the hubs 77, 78 and 79, respectively of the brushes 13, 14 and 15, respectively.

Figure 19:
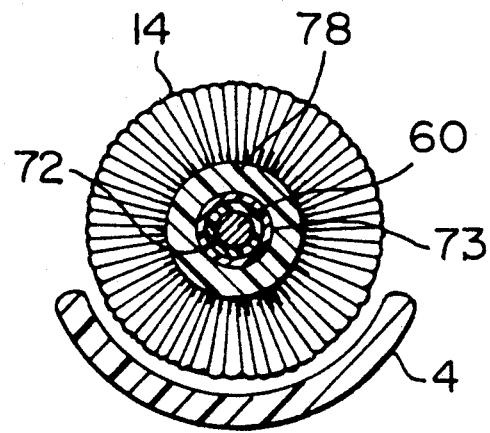
FIG. 19 is a cross section taken generally along line XIX—XIX of FIG. 18.

As best shown in FIGS. 2 and 19, the outer free end of the brush carrier is open throughout most of the area thereof, so that the brushes 12, 13, 14 and 15 are unobstructed.

In operation, the brushes 12 and 14 are rotated in one direction (indicated by arrows in FIG. 2) by the shafts 41 and the associated gears 42 and 43 (FIG. 9) and 50 and 52 (FIG. 11). The brushes 13 and 15 are rotated in the opposite direction by the shafts 38, and the associated gears 47 and 48 (FIG. 10) and 55 and 56 (FIG. 12). The counter rotating brushes simulate the up and down motion encouraged by dentists.

What I claim is:

1. A rotary toothbrush comprising elongated casing means; a plurality of annular brush means rotatably mounted in one at least partially open end of said casing means for rotation around a single casing drive means in the casing means for rotating said brush means, said drive means includes motor means in said casing means; gear means for rotation by said motor means; and a plurality of coaxial shaft means connecting said gear means to said brush means, whereby each said brush means can be rotated independently of any other said brush means; and transmission means connecting said drive means to said brush means for rotating at least one said brush means in one direction, and rotating at least one other said brush means in the opposite direction.

2. A rotary toothbrush according to claim 1, wherein said casing means includes elongated, cylindrical handle means, an enlarged bottom free end on said casing means preventing insertion thereof into a charging stand; and brush carrier means connected to the upper end of said handle means, said brush carrier means having a smaller diameter than said handle means for insertion into a charging stand.

3. A rotary toothbrush according to claim 1, wherein said gear means includes first gear means for driving by said motor means and determining the speed of rotation of said brush means; second gear means connected to said first gear means for rotating selected of said shaft means in one direction; and third gear means for rotating the remainder of said shaft means in the opposite direction.

4. A rotary toothbrush according to claim 3, wherein said shaft means includes first coaxial shaft means connected to said second and third gear means; second coaxial shaft means carrying said brush means; and coupler means interconnecting said first and second coaxial shaft means.

* * * * *